US006572552B2

(12) United States Patent
Fukukita

(10) Patent No.: US 6,572,552 B2
(45) Date of Patent: Jun. 3, 2003

(54) ULTRASONIC DIAGNOSTIC APPARATUS

(75) Inventor: Hiroshi Fukukita, Tokyo (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 2 days.

(21) Appl. No.: 09/919,000

(22) Filed: Jul. 31, 2001

(65) Prior Publication Data

US 2002/0042572 A1 Apr. 11, 2002

(30) Foreign Application Priority Data

Aug. 2, 2000 (JP) ....................................... 2000-234854

(51) Int. Cl.[7] .................................................. A61B 8/14

(52) U.S. Cl. ....................... 600/459; 310/320; 310/322; 367/140; 367/153

(58) Field of Search .......................... 600/459; 310/320, 310/334, 336, 322; 367/140, 153

(56) References Cited

U.S. PATENT DOCUMENTS 5,415,175 A * 5/1995 Hanafy et al. .............. 600/459
5,724,976 A * 3/1998 Mine et al. ................. 600/459
5,945,770 A * 8/1999 Hanafy ....................... 310/322

* cited by examiner

*Primary Examiner*—Marvin M. Lateef
*Assistant Examiner*—Ruby Jain
(74) *Attorney, Agent, or Firm*—Pearne & Gordon LLP

(57) ABSTRACT

An ultrasonic diagnostic apparatus for observing a detectable object to be ultrasonically diagnosed. The apparatus includes an ultrasonically diagnostic probe unit for probing the object with ultrasonic waves in response to input pulse signals and with an ultrasonic echo from the object, a signal transmitting unit to generate the input pulse signals, a signal receiving unit for receiving the ultrasonic echo and processing output signals to be converted into an image of the object, and a display unit to display the image. The ultrasonically diagnostic probe unit comprises an oscillation body having a pair of piezoelectric layers, an intermediate layer sandwiched by the piezoelectric layers, an acoustic lens body operative to focus the ultrasonic waves to be emitted to and reflected by the object, and a supporting body having the oscillation body mounted thereon, thereby making it possible to provide an ultrasonic diagnostic apparatus with a readily machinable oscillation body and to facilitate the machining and adhesive processes of the oscillation body.

15 Claims, 10 Drawing Sheets

ULTRASONIC DIAGNOSTIC APPARATUS

BACKGROUND OF THE INVENTION

1. Field of the Invention

The present invention relates to an ultrasonic diagnostic apparatus equipped with a probe unit including an oscillation body operable to control the aperture of transmission and reception of the ultrasonic waves to be emitted to and reflected by the object being observed.

2. Description of the Related Art

Conventionally, there have been provided an ultrasonic diagnostic apparatus designed to control the aperture of the ultrasound beam. The ultrasonic diagnostic apparatus of this type is disclosed in Japanese Patent Laying-open Publication No. 7-107595 and shown in FIG. 10. This apparatus comprises a piezoelectric layer 91, an acoustic matching layer 92, and a backing block 93 supporting the layers 91 and 92. The piezoelectric layer 91 is divided into a plurality of segments arranged in the azimuthal direction Da of the probe unit. The thickness of the piezoelectric layer 91 in the minor axis direction Dm is small in the center of the piezoelectric layer 91 but large at each end of the piezoelectric layer 91. The probe unit of the ultrasonic diagnostic apparatus is therefore capable of obtaining a broadband frequency characteristic because of the fact that the center portion of each segment mainly senses high frequency ultrasonic waves while the end portion of each segment mainly senses relatively low frequency ultrasonic waves. The aperture of the piezoelectric layer 91 of the probe unit, i.e., the aperture for transmitting and receiving the ultrasonic waves is controlled by the signal transmitting unit 95 and the signal receiving unit 96 in inverse proportion to the frequency of the ultrasonic waves passing through the piezoelectric layer 91. This results in the fact that the image resolution of the ultrasonic diagnostic apparatus is improved at any focal distance of the ultrasonic diagnostic apparatus.

The conventional ultrasonic diagnostic apparatus thus constructed in the above, however, encounters such a problem that the piezoelectric layers are required respectively to be machined in the shape of a plano-concave element and to be precisely laminated in their adhesive processes.

The present invention contemplates resolution of such problems.

SUMMARY OF THE INVENTION

It is therefore an object of the present invention to provide an ultrasonic diagnostic apparatus with a readily machinable oscillation body without declining the resolution of the ultrasonic diagnostic apparatus at any focal distance and to facilitate the machining and adhesive processes of the oscillation body.

According to one aspect of the present invention, there is provided an ultrasonic diagnostic apparatus for observing a detectable object to be ultrasonically diagnosed, comprising: an ultrasonically diagnostic probe unit for probing the detectable object with the ultrasonic waves emitted to the detectable object in response to input pulse signals and with the ultrasonic echo from the detectable object; a signal transmitting unit operatively connected with the ultrasonic diagnostic probe unit to generate the input pulse signals to be transmitted into the ultrasonic waves by the ultrasonically diagnostic probe unit; a signal receiving unit operatively connected with the ultrasonically diagnostic probe unit for receiving the ultrasonic echo from the detectable object and processing output signals to be converted into the image of the detectable object being observed; a display unit operatively connected with the signal receiving unit to display the image of the detectable object on the basis of the output signals from the signal receiving unit to ensure the ultrasonically diagnosed state of the detectable object. The ultrasonically diagnostic probe unit comprises an oscillation body having a pair of piezoelectric layers, an intermediate layer sandwiched by the piezoelectric layers, an acoustic lens body operative to focus the ultrasonic waves to be emitted to and reflected by the detectable object, and a supporting body having the oscillation body mounted thereon to ensure that the detectable object is probed by the oscillation body to be ultrasonically diagnosed with the display unit.

The signal receiving unit may have a wave propagation direction along which the ultrasonic waves propagate, an azimuthal direction perpendicular to the wave propagation direction, and a minor axis direction perpendicular to the wave propagation direction and the azimuthal direction, and one of the piezoelectric layers of the oscillation body may have a central portion extending along the azimuthal direction and a pair of end portions integrally formed with the central portion. In this case, the total thickness of the end portions of the piezoelectric layers is smaller than that of the central portion of the piezoelectric layer, and the thickness of each end portion of the intermediate layer is larger than that of the central portion of the intermediate layer.

In the above ultrasonic diagnostic apparatus, the piezoelectric layers of the oscillation body may have respective cross sections taken on the plane parallel to the wave propagation direction and the azimuthal direction and each including a truncated convex portion and a rectangular portion integrally formed with the truncated convex portion, the truncated convex portion having a bulged contour constituted by a flat center surface portion and a pair of inclined surface portions having the center surface portion positioned therebetween in the minor axis direction and each inclined to have its first end connected to the center surface portion and its second end connected to the cross sectional contour of the rectangular portion. In this case, the center surface portions of the piezoelectric layers are held in buttjoint engagement with each other and the intermediate layer has a pair of wedge portions opposed to each other and outwardly gradually thickening as the corresponding two positions of the wedge portions space apart from each other.

The truncated convex portions of the piezoelectric layers may be held in contact with each other at the flat center surface portions of the truncated convex portions.

The piezoelectric layers may respectively have first side surface portions formed with a plurality of grooves and second side surface portions opposed to each other, and the first side surface portions may be segmented into a plurality of element regions with the grooves spaced apart from one another in the azimuthal direction.

In the case that the oscillation body has three directions consisting of a wave propagation direction, an azimuthal direction and a minor axis direction and that the intermediate layer of the oscillation body has a central portion extending along the azimuthal direction and a pair of end portions and integrally formed with the central portion, the thickness of the end portion of the intermediate layer may be mechanically equal to that of the central portion of the intermediate layer under the condition that the central portion of the intermediate layer has predetermined acoustic impedance ultrasonically different from that of each end portion of the intermediate layer.

In this case, the intermediate layer of the oscillation body may have different material portions different in acoustic impedance and adjacent to one another. The different material portions preferably include a high impedance portion having predetermined acoustic impedance and a pair of low impedance portions having respective acoustic impedance lower than that of the high impedance portion. Further, the intermediate layer of the oscillation body may have a pair of intermediate impedance portions each having acoustic impedance lower than that of the high impedance portion and higher than that of the low impedance portion. In this case, the intermediate impedance portions are provided preferably between the high impedance portion and the low impedance portion in the minor axis direction.

It is preferable that the piezoelectric layers of the oscillation body be made of a ceramic material and that the intermediate layer of the oscillation body have acoustic impedance of 2 through 8 Mrayl. The intermediate layer may be made of a resin.

It is also preferable that the oscillation body further include an acoustic matching layer provided between the acoustic lens body and the piezoelectric layer facing to the acoustic lens body. In this case, the matching layer preferably serves as the quarter wave plate.

The acoustic lens may have a first lens portion of a short focal distance and a second lens portion of the focal distance longer than that of the first lens portion, the second lens portion having the first lens portion positioned therein.

The ultrasonic diagnostic apparatus according to the present invention may further comprise: a first lead member electrically connected to the interior surfaces of the truncated convex portions of the piezoelectric layers; and a second lead member electrically connected to both of the exterior surfaces of the piezoelectric layers, and one of the first and second lead members is connectable to the ground and the other of the first and second lead members being connectable to the signal transmitting unit and signal receiving unit.

The signal transmitting unit may be operative to generate the input pulse signals as the impulse signals or the chirp pulse signals to be transmitted into the ultrasonic waves by the ultrasonically diagnostic probe unit.

The signal receiving unit may have a dynamic filter having the output signals pass therethrough and changed from a high frequency range to a relatively low frequency range.

The central portion of the intermediate layer may be constituted by a medium having acoustic impedance substantially equal to that of anyone of the piezoelectric layer, and the end portion of the intermediate layer is constituted by a medium having acoustic impedance substantially equal to or less than that of anyone of the piezoelectric layer.

BRIEF DESCRIPTION OF THE DRAWINGS

The features and advantages of the ultrasonic diagnostic apparatus according to the present invention will be more clearly understood from the following description taken in conjunction with the accompanying drawings in which.

DESCRIPTION OF THE PREFERRED EMBODIMENTS

Referring to FIGS. 1 to 6 of the drawings, there is shown a first preferred embodiment of the ultrasonic diagnostic apparatus embodying the present invention which comprises an ultrasonically diagnostic probe unit 5 for emitting ultrasonic waves to the detectable object 50 in response to input pulse signals, and receiving an ultrasonic echo from the detectable object 50 to probe the detectable object 50.

Figure 1:
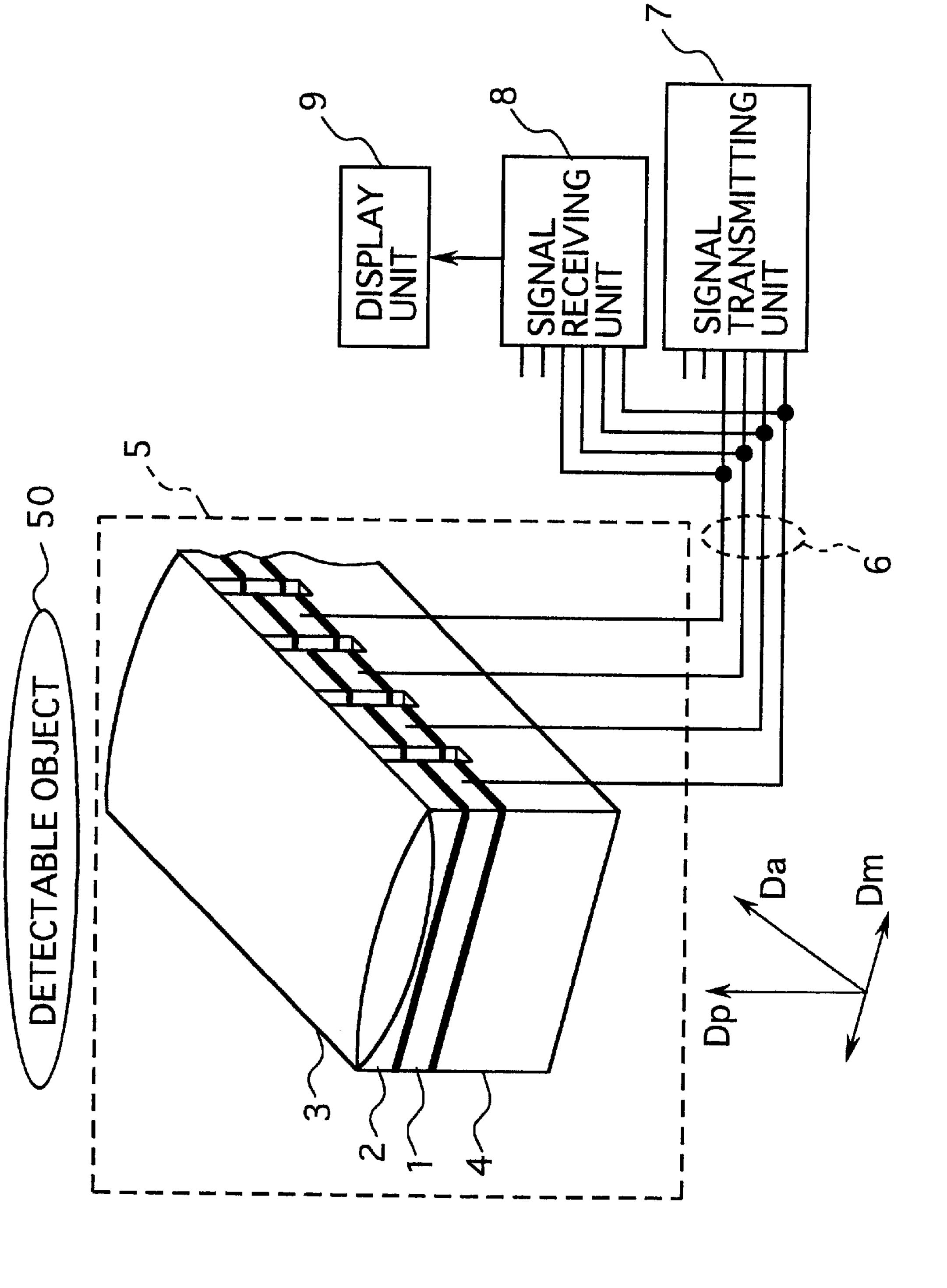
FIG. 1 is a schematic diagram of a first embodiment of the ultrasonic diagnostic apparatus according to the present invention.

As shown in FIG. 1, the ultrasonic diagnostic apparatus further comprises a set of signal lines 6, a signal transmitting unit 7, a signal receiving unit 8 and a display unit 9. The signal transmitting unit 7 is adapted to generate the input pulses and operatively connected with the ultrasonic diagnostic probe unit 5 to have the input pulse signals transmitted into the ultrasonic waves by the ultrasonically diagnostic probe unit 5. The signal receiving unit 8 is operatively connected with the ultrasonically diagnostic probe unit 5 through the signal lines 6 for receiving echo signals varied with the ultrasonic echo from the detectable object 50. The receiving unit 8 also is adapted to process the echo signals from the ultrasonic diagnostic probe unit 5 in order to generate output signals to be converted into the image of the detectable object 50 being observed. The signal receiving unit 8 also includes a dynamic filter not shown in the drawing.

The display unit 9 is operatively connected with the signal receiving unit 8 to display the image of the detectable object 50, on the basis of the output signals from the signal receiving unit 8, sufficient to ensure the ultrasonically diagnosed state of the detectable object 50. The dynamic filter of the signal receiving unit 8 has the output signals outputted so as to change the frequency range of the output signals from a predetermined high frequency range to a relatively low frequency range.

Figure 2A:
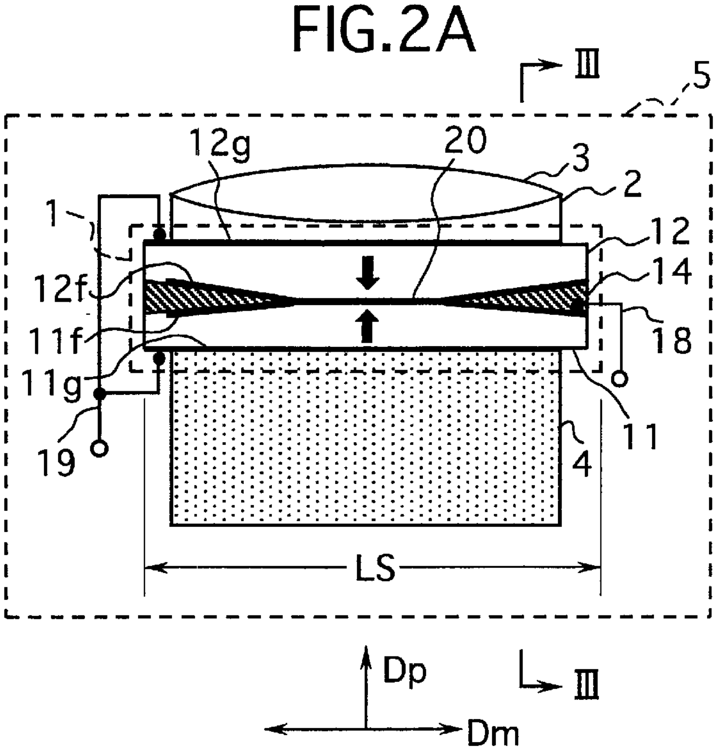
FIG. 2A is a cross-sectional view of the first embodiment of the ultrasonic diagnostic apparatus.

As shown in FIGS. 1 and 2A, the ultrasonically diagnostic probe unit 5 comprises an oscillation body 1 having a pair of piezoelectric layers 11 and 12 facing to each other, and an intermediate layer 14 provided between and sandwiched by the piezoelectric layers 11 and 12. The ultrasonic diagnostic apparatus further comprises an acoustic lens body 3 operative to focus the ultrasonic waves from the oscillation body 1 and being emitted to and reflected by the detectable object 50, an acoustic matching layer 2 provided between the acoustic lens body 3 and the piezoelectric layer 12 facing to the acoustic lens body 3, and a supporting body 4 having the oscillation body 1 mounted thereon to ensure that the detectable object 50 is probed by the ultrasonic diagnostic probe unit 5 to be ultrasonically diagnosed with the display unit 9. The piezoelectric layer 11 has an interior surface having an electrode 11*f* mounted thereon, and an exterior surface having an electrode 11*g* mounted thereon, while the piezoelectric layer 12 has an interior surface having an electrode 12*f* mounted thereon, and an exterior surface having an electrode 12*g* mounted thereon. The matching layer 2 is adapted to serve as the quarter wave plate which has the thickness depending upon the position in the azimuthal direction Da with the wavelength of the ultrasonic waves passing through each portion of the matching layer 2.

The oscillation body 1 is operative to emit the ultrasonic waves and to receive the ultrasonic echo from the detectable object 50 such as intestinal organs being observed while the input pulse signals are inputted from the signal transmitting unit 7 through the signal lines 6. Each of the piezoelectric layers 11 and 12 is made of a piezoelectric ceramic material or the like. The acoustic matching layer 2 is designed to serve as the quarter-wave plate based on the dominant fundamental harmonic frequency of the oscillation body 1. The thickness of the acoustic matching layer 2 is set at a relatively small value in the center of the oscillation body 1, but is set at a relatively large value at each end of the oscillation body 1, since the acoustic matching layer 2 serves as the quarter-wave plate with respect to the dominant fundamental harmonic frequency of the oscillation body 1.

The piezoelectric layers 11 and 12 of the oscillation body 1 have respective cross sections taken on the plane parallel to the wave propagation direction Dp and the azimuthal direction Da. The total thickness of the one end portions 11*b* and 12*b* of the piezoelectric layers 11 and 12, or the total thickness of the other end portions 11*c* and 12*c* of the piezoelectric layers 11 and 12 is smaller than the total thickness of the central portions 11*a* and 12*a* of the piezoelectric layers 11 and 12. The thickness "Tg" (see FIG. 3) of each end portion 14*b* or 14*c* of the intermediate layer 14, on the other hand, is larger than that of the central portion 14*a* of the intermediate layer 14. The central portion 14*a* of the intermediate layer 14 is thin sufficient to have the piezoelectric layers 11 and 12 held in contact with each other.

Figure 2B:
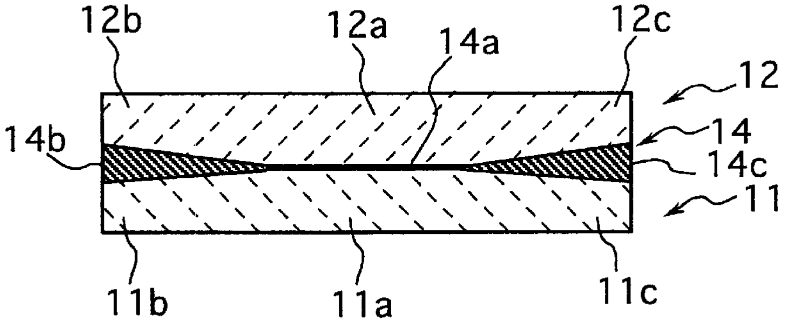
FIG. 2B is an enlarged cross-sectional view of an oscillation body shown in FIG. 2A and forming part of the first embodiment of the ultrasonic diagnostic apparatus.
Figure 2C:
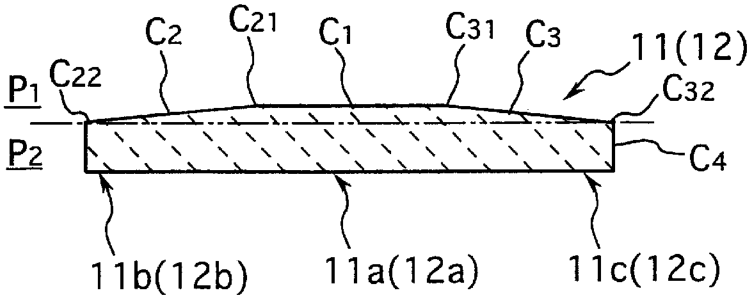
FIG. 2C is an enlarged cross-sectional view of a piezoelectric element forming part of the oscillation body shown in FIG. 2A.

Further, each of the piezoelectric layers 11 and 12 includes a truncated convex portion P1 and a rectangular portion P2 adjacent to and integrally formed with the truncated convex portion P1, and the truncated convex portion P1 has a bulged contour constituted by a flat center surface portion C1 and a pair of inclined surface portions C2 and C3 having the center surface portion C1 positioned therebetween in the minor axis direction Dm. The surface portions C2 and C3 respectively incline with respect to the flat center surface portion C1 to have their first end C21 and C31 connected to the center surface portion C1, and their second end C22 and C32 connected to the cross sectional contour C4 of the rectangular portion P2. As shown in FIGS. 2*a* and 2*b*, the center surface portions C1 of the piezoelectric layers 11 and 12 are held in buttjoint engagement with each other so that the intermediate layer 14 of the oscillation body 1 has their end portions 14*b* and 14*c* as a pair of wedge portions opposed to each other. The flat central surface portion C1, i.e., each of the flat interior surfaces 20 of the piezoelectric layers 11 and 12, has a width approximately equal to 10 through 20% length of the piezoelectric layer 11 or 12 in the minor axis direction Dm.

Each of the wedge portions 14*b* and 14*c* is made of an acoustic transmissible medium, such as for example a resin having an acoustic impedance of 2 through 8 Mrayl or the same degree lower than that of the piezoelectric ceramic material. The wedge portions 14*b* and 14*c* have cross-sections similar in shape to each other, and the thickness "Tg" of the wedge portion 14*b* or 14*c* is gradually outwardly increased in response to the distance between the corresponding two positions of the wedge portions 14*b* and 14*c* spaced apart from each other in the minor direction Dm.

In this embodiment, the truncated convex portions P1 of the piezoelectric layers 11 and 12 are held in contact with each other at the flat center surface portion C1 of the truncated convex portion P1. The piezoelectric layers 11 and 12 thus have respective plano-convex cross-sections each perpendicular to the azimuthal direction Da of the ultrasonic diagnostic probe unit 5.

Figure 3:
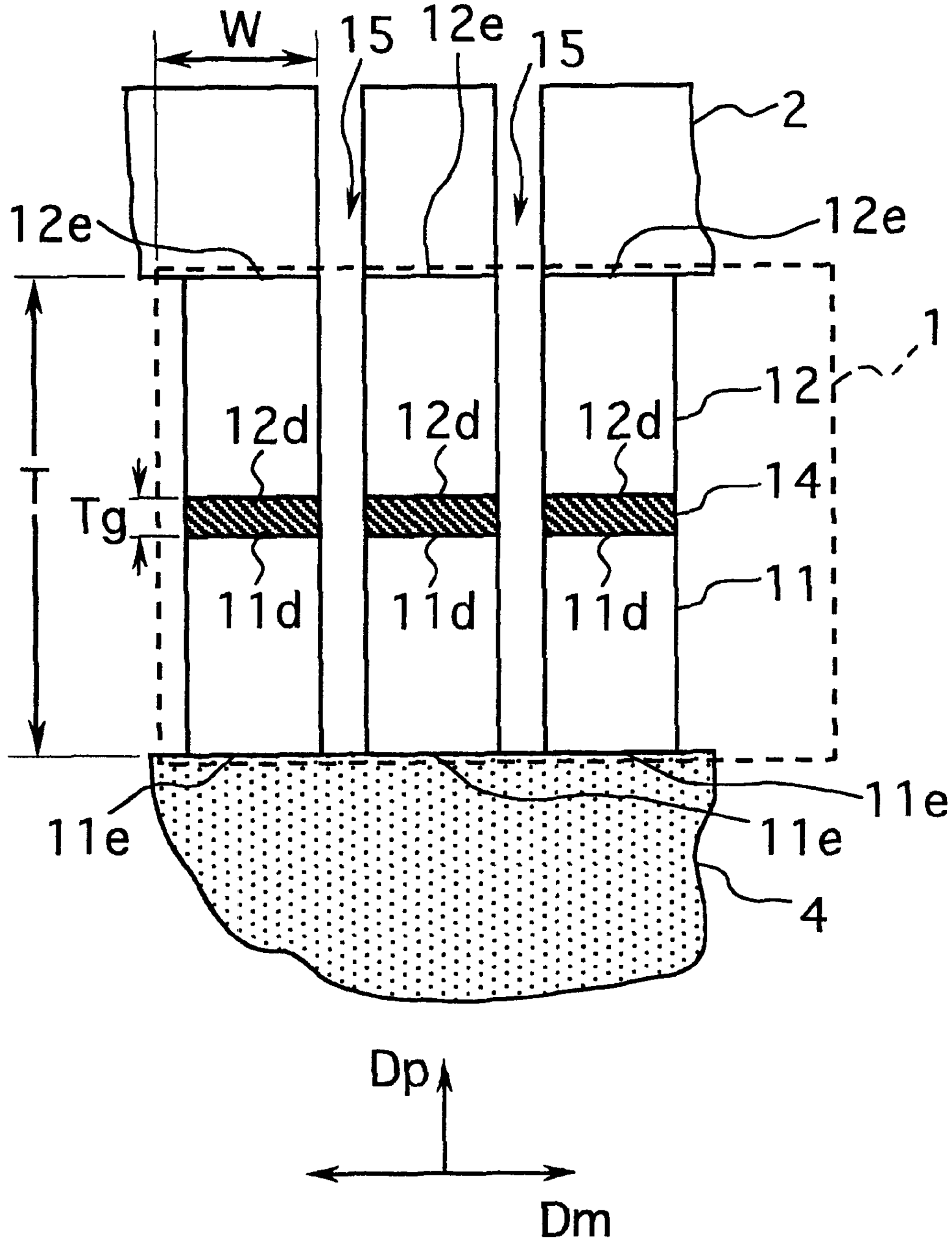
FIG. 3 is an enlarged sectional view taken along the line III—III in FIG. 2A.

As shown in FIG. 3, the piezoelectric layer 11 has on both face sides an interior surface portion lid and an exterior surface portion lie supported on the supporting body 4, while the piezoelectric layer 12 has on both face sides an interior surface portion 12*d* facing to the interior surface portion lid of the piezo electric layer ii and an exterior surface portion 12*e* having the matching layer 2 mounted thereon. In addition, the piezoelectric layers 11 and 12 are divided into a plurality of segments spaced apart from one another with a plurality of grooves 15 each formed between the segments. The interior surface portions 11*d* and 12*d* of the piezoelectric layers 11 and 12 are therefore segmented into a plurality of element regions each having a width "W" with the grooves 15 spaced apart from one another in the azimuthal direction Da.

The ultrasonic diagnostic apparatus further comprises a supporting body 4 serving as a backward load element and supporting the piezoelectric layer 11 on one side of the oscillation body 1. The exterior surface portion 12*e* of the piezoelectric element 12 is formed to be flat and supports the acoustic matching layer 2 facing to the acoustic lens body 3.

On the flat interior surfaces 20 corresponding to the flat central surface portion C1 of the piezoelectric layers 11 and 12, there are provided first and second lead members 18 and

19. (See FIG. 2A) One of the first and second lead members 18 and 19, e.g. lead member 18, is connectable to the ground and the other of the first and second lead members 18 and 19, e.g. lead member 19, is connectable through the signal lines 6 to the signal transmitting unit 7 and signal receiving unit 8.

In the above-mentioned ultrasonic diagnostic apparatus, the signal transmitting unit 7 is operated firstly to generate input pulse signals for driving the ultrasonic diagnostic probe unit 5. The input pulse signals are transmitted to the oscillation body 1 of the ultrasonic diagnostic probe unit 5 as the impulse signals, the chirp pulse signals or the likes.

At this time, the oscillation body 1 is driven by the input pulse signals to emit the ultrasonic waves. The ultrasonic waves emitted from the oscillation body 1 are transmitted through the acoustic matching layer 2 and discharged from the acoustic lens 3 to the detectable object 50 in the form of the ultrasound pulses. The speed of the ultrasound discharged from the oscillation body 1 is approximately the same as the speed of the ultrasound passing through the above piezoelectric ceramic material of the center portions 11*a* and 12*a* of the oscillation body 1, but in each end portion of the oscillation body 1 substantially lower than the speed of the ultrasound passing through the above piezoelectric ceramic material. The resonant frequency of the oscillation body 1 is therefore reduced to a relatively low frequency at each end portion of the oscillation body 1, while the resonant frequency of the oscillation body 1 is maintained at a certain relatively high frequency in the center of the oscillation body 1. This results in the fact that the ultrasonic diagnostic prove unit 5 has a broadband acoustic characteristic.

As aforesaid, the ultrasonic waves emitted from the oscillation body 1 are outputted from the acoustic lens 3 in the form of the ultrasound pulses. The ultrasound pulses include a plurality of high and low frequency components focused by the acoustic lens 3 on the detectable object 50 as the ultrasound beam. In the case that the acoustic lens 3 is operated through the signal lines 6 to have a relatively small aperture of the ultrasound beam, the high frequency components of the ultrasonic waves are mainly focused in the center portion and at a relatively short focal distance as will be seen by the legend "Fnear" in FIG. 6A to have a predetermined small diameter of the ultrasound beam composed of the high frequency components. On the other hand, in the case that the acoustic lens 3 is operated through the signal lines 6 to have a relatively large aperture of the ultrasound beam, the relatively low frequency components of the ultrasonic waves are focused at a relatively long focal distance by the acoustic lens 3, as shown by the legend "Ffar" in FIG. 6A, to have a certain small diameter of the ultrasound beam composed of the low frequency components. In other words, the acoustic lens 3 has a central first lens portion of a short focal distance while the oscillation body 1 has a relatively small aperture, and the acoustic lens 3 has a second lens portion of the focal distance larger in area from the first lens portion and longer than that of said first lens portion while the oscillation body 1 has a relatively large aperture. The second lens portion therefore has the first lens portion positioned therein.

The focused ultrasonic waves are dispersed in and reflected by the detectable object 50 as an ultrasonic echo. The ultrasonic echo is then received by the ultrasonic diagnostic probe unit 5 and transferred into the echo signals by the signal receiving unit 8. The echo signals are filtered by the dynamic filter of the signal receiving unit 8 and have their relatively low frequency components. This enables to improve the image resolution of the ultrasonic diagnostic apparatus in the minor axis direction when the display unit 9 displays the image.

More specifically, the dominant filtering frequency of the signal receiving unit 8 is set at a relatively high frequency to have the high frequency components of the ultrasonic waves transmitted through the oscillation body 1 and the signal receiving unit 8 in a given first time interval immediately after the input pulse signals are generated by the signal transmitting unit 7. In contrast, the dominant filtering frequency of the signal receiving unit 8 is set at a relatively low frequency to have the low frequency components of the ultrasonic waves transmitted through the oscillation body 1 and the signal receiving unit 8 in a given second time interval after the first time interval. In the above first time interval, the echo signals corresponding to the high frequency components of the ultrasonic echo are allowed to pass through the dynamic band pass filter of the signal receiving unit 8, while on the other hand in the above second time interval, the echo signals corresponding to the low frequency components of the ultrasonic echo are allowed to pass through the dynamic band pass filter of the signal receiving unit 8. As a consequence, the resolution of the image in the minor axis direction is sufficiently improved at any focal distance.

Figure 4:
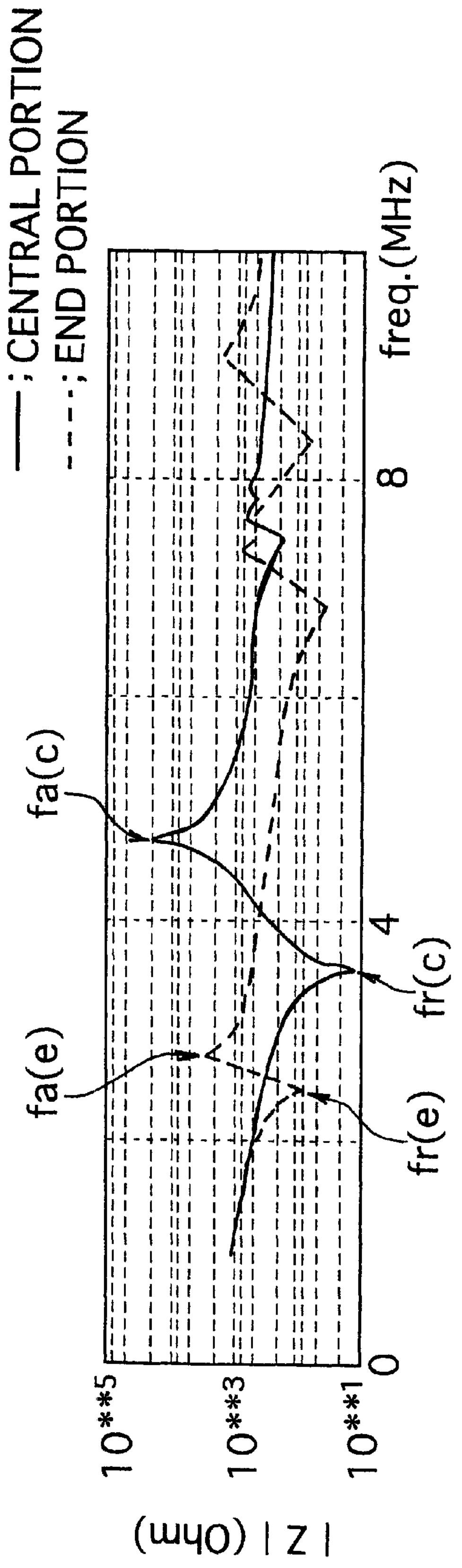
FIG. 4 is a graph depicting the absolute of the impedance "Z" of the oscillation body with respect to the frequency of ultrasonic waves and showing the frequency characteristic of the oscillation body.

FIG. 4 depicts the absolute of the impedance "Z" of the oscillation body 1 varied in response to the frequency of the ultrasonic waves and shows the frequency characteristic of the oscillation body 1. In this case, the intermediate layer 14 is made of a resin having an acoustic impedance of 7 Mrayl, and the piezoelectric layers 11 and 12 are each made of PZT ceramic material or the like. The thickness "T" of the oscillation body 1 is set at 400 micron, the width "W" of the each element region of the oscillation body 1 is set at 200 micron, and the thickness of the center portion 14*a* of the intermediate layer 14 is set at zero (See solid line shown in FIG. 4) or 20 micron. (See dashed line shown in FIG. 4)

The resonant frequency fr(c) is approximately equal to 3.5 MHz higher than the resonant frequency fr(e) of 2.4 MHz. That is, the center portion of the oscillation body 1 has a frequency constant varied in response to the resonant frequency of the center portion of the oscillation body 1. The frequency constant of the center portion of the oscillation body 1 is larger than that of the end portion of the oscillation body 1. Incidentally, the end portion of the oscillation body 1 has the electromechanical coupling constant "k"=70% calculated on the basis of the anti-resonant frequency "fa(e) "=3.9 MHz and resonant frequency "fr(e)". The frequency constant of the end portion of the oscillation body 1 is relatively small in comparison with the electromechanical coupling constant "k"=50% calculated on the basis of the anti-resonant frequency "fa(c)"=4.7 MHz and resonant frequency "fr(c)".

The ultrasound pulses radiated from the end portion of the oscillation body 1 therefore have a bandwidth and an amplitude narrower than those of the ultrasound pulses radiated from the center portion of the oscillation body 1. The differences of the bandwidth and amplitude between the ultrasound pulses emitted from the center and end portions of the oscillation body 1 render it possible to obtain a suitable response of the ultrasonic echo without excessively increasing the amplitude of the response of the oscillation body 1. This means that preventing the respondent amplitude of the end portion is equivalent to weight the aperture of the oscillation body 1 and improves the resolution of the ultrasonic diagnostic apparatus.

Figure 5:
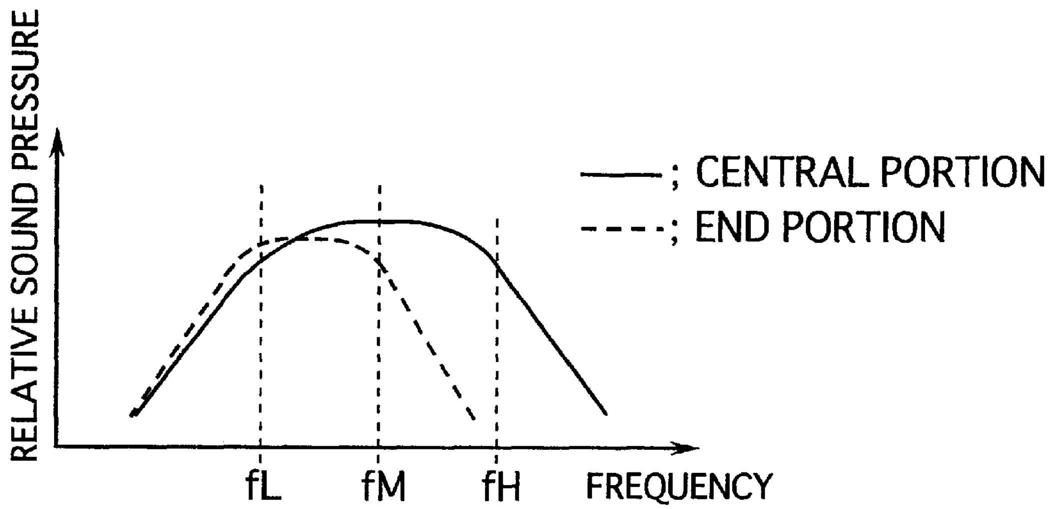
FIG. 5 is a graph illustrating the relative sound pressure with respect to the frequency of the echo reflected by an detectable object and showing the frequency characteristic of the center and both end portions of the oscillation body.

FIG. 5 illustrates the relative sound pressure with respect to the frequency of the ultrasonic echo reflected by the detectable object 50, and shows the frequency characteristic of the center and both end portions of the oscillation body 1. In this figure, the frequency characteristic of the center portion of the oscillation body 1 is shown by a solid line, and the frequency characteristic of each end portion of the oscillation body 1 is shown by a dashed line. It is understood from the solid line shown in FIG. 5 that the center portion of the oscillation body 1 has the frequency characteristic in which the relative sound pressure is varied with the frequency of the ultrasonic echo from the detectable object 50 to have a focused high pressure region with a relatively wide bandwidth between vertical dotted frequency lines fL and fH. It is also understood from the dashed line that each of the end portions of the oscillation body 1 has the frequency characteristic in which the relative sound pressure is varied with the frequency of the ultrasonic echo from the detectable object 50 to have a focused high pressure region lower in sound pressure than that of the above focused high pressure region shown by the solid line. In the case that the frequency of the ultrasonic echo is relatively high, the echo signals corresponding to the ultrasonic echo are outputted from the center portion of the oscillation body 1. Contrary to the above, if in the case that the frequency of the ultrasonic echo is relatively low, the echo signals corresponding to the ultrasonic echo are outputted from the end portions and the central portions of the oscillation body 1.

Figure 6B:
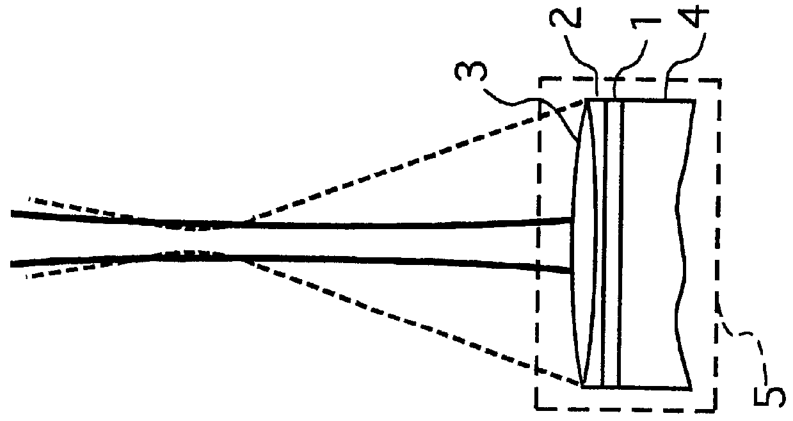
FIG. 6B is an explanatory side view of the oscillation body showing the ultrasound beams emitted from the oscillation body and the echo beam reflected by the object being observed.
Figure 6A:
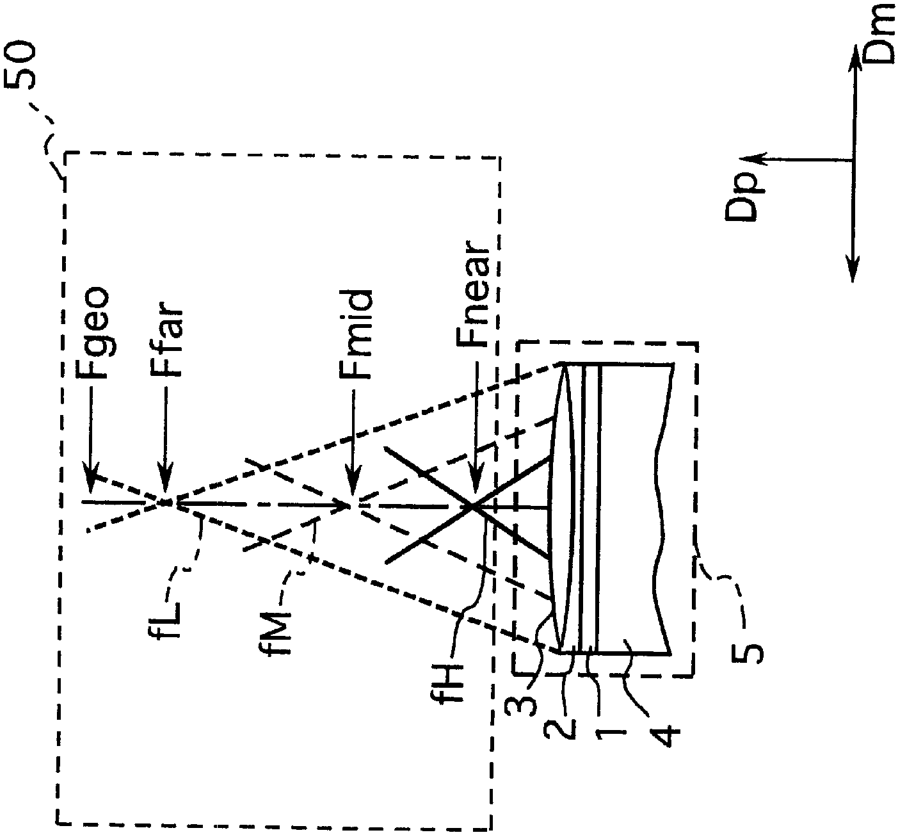
FIG. 6A is an explanatory side view of the oscillation body showing ultrasound beams and their different focal points varied in response to the aperture of the oscillation body.

FIG. 6A shows the sound field of the ultrasonic waves emitted from the oscillation body 1. As shown in this figure, the ultrasonic waves includes three frequency components "fH", "fL" and "fM" relatively high, low and middle in frequency and three focal points "Fnear", "Fmid" and "Ffar" of the frequency components "fH", "fL" and "fM" different in focal distance and determined by the oscillation body 1 in proportion to the aperture of the oscillation body. In the present embodiment, the acoustic lens 3 has a focal point set at the point "Fgeo" shown in FIG. 6. The acoustic lens 3 may be different from the above one in structure and operative to focus the ultrasonic echo from the detectable object 50 with respective different focal points.

When the aperture of the oscillation body 1 is suitably set at any focal distance, the ultrasonic echo reflected by the detectable object 50 is distributed into a beam as shown in FIG. 6B by a thick solid line. This leads to the fact that the diameter of the echo beam is reduced and the resolution of the ultrasonic diagnostic apparatus in the azimuthal direction is improved.

It will be understood from the foregoing description that the piezoelectric layers 11 and 12 of the oscillation body 1 are easily machinable and capable of facilitating the machining and adhesive processes of the oscillation body 1 because of the fact that the piezoelectric layers 11 and 12 have respective bulged contour and held in contact with each other at their flat center surface portions C1 and that the intermediate layers 14 is provided between the piezoelectric layers 11 and 12. It is therefore possible not only to provide the ultrasonic diagnostic apparatus with the ultrasonic diagnostic prove unit 5 and oscillation body 1 readily machinable and aperture controllable, but also to facilitate the machining and adhesive processes of the oscillation body without declining the resolution of the ultrasonic diagnostic apparatus at any focal distance.

The above oscillation body 1 may be different in structure so as to include additional piezoelectric layer or layers under the condition that the total thickness of the piezoelectric layers of the oscillation body 1 is relatively large at the center portion of the oscillation body 1 and relatively small at the end portions of the oscillation body 1.

It further will be understood that the ultrasonic diagnostic apparatus according to the present invention overcomes the aforesaid remaining problems in the prior art ultrasonic diagnostic apparatus.

The above first embodiment of the ultrasonic diagnostic apparatus may be replaced by the second embodiment of the present invention in order to attain the object of this invention as will be understood from the following description.

Figure 7:
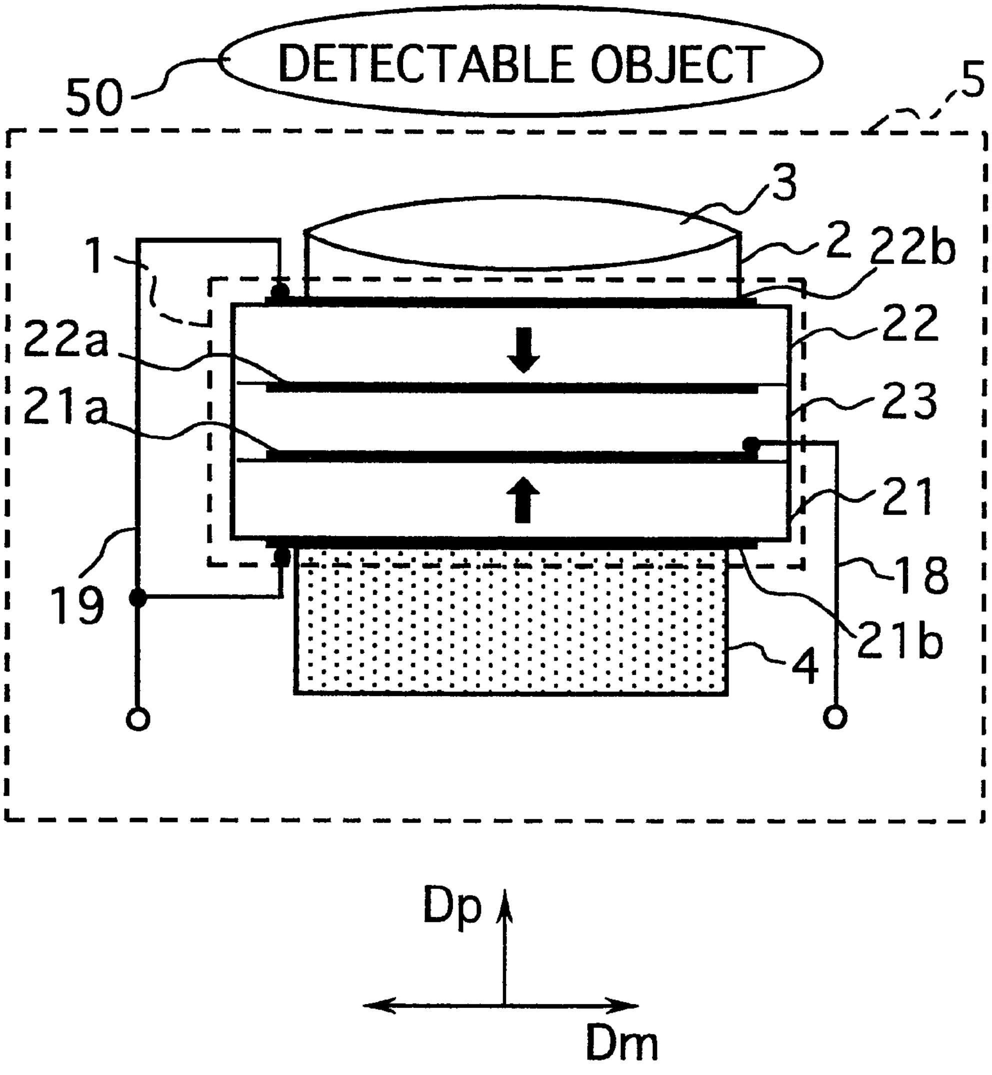
FIG. 7 is a cross-sectional view of a second embodiment of the ultrasonic diagnostic apparatus according to the present invention.

Referring to FIGS. 7 and 8 of the drawings, there is shown a second preferred embodiment of the ultrasonic diagnostic apparatus embodying the present invention. The ultrasonic diagnostic apparatus in the second embodiment is constructed in the similar manner to the aforesaid first embodiment except for the difference in structure of the oscillation body. For this reason, the following description will be briefly made with the reference numerals partly the same as those of the above constitutional elements of the first embodiment.

The ultrasonically diagnostic probe unit 5 comprises an oscillation body 1 having a pair of piezoelectric layers 21 and 22, and an intermediate layer 23 provided between and sandwiched by the piezoelectric layers 21 and 22. The ultrasonically diagnostic probe unit 5 further comprises an acoustic lens body 3 mounted on the oscillation body 1 to focus the ultrasonic waves to be emitted to and reflected by the detectable object 50, an acoustic matching layer 2 provided between the acoustic lens body 3 and the piezoelectric layer 22 facing to the acoustic lens body 3, and a supporting body 4 having the oscillation body 1 mounted thereon to ensure that the detectable object 50 is probed by the oscillation body 1. The ultrasonically diagnostic probe unit 5 is operative to probe the detectable object 50 in the same manner as that of the above first embodiment. The piezoelectric layer 21 has an interior surface having an electrode 21*a* mounted thereon and an exterior surface having an electrode 21*b* mounted thereon, while the piezoelectric layer 22 has an interior surface having an electrode 22*a* mounted thereon and an exterior surface having an electrode 22*b* mounted thereon.

The oscillation body 1 has three different directions consisting of a wave propagation direction Dp, an azimuthal direction Da and a minor axis direction Dm The ultrasonic waves propagate in the wave propagation direction Dp, the oscillation body 1 is divided into a plurality segments spaced apart from one another in the azimuthal direction Da. The minor axis direction Dm is perpendicular to the wave propagation direction Dp and the azimuthal direction Da. The supporting body 4 mechanically supports the oscillation body 1.

The oscillation body 1 is constituted by a pair of piezoelectric layers 21 and 22, and an intermediate layer 23 provided between and sandwiched by the piezoelectric layers 21 and 22. The detectable object 50 is probed by the ultrasonic diagnostic probe unit 5 to be ultrasonically diagnosed with the display unit 9.

In the case that the thickness of the oscillation body 1 equals to 400 micron, and the thickness of the intermediate layer 23 equals to 10 micron and that the piezoelectric layers 21 and 22 are each made of a piezoelectric ceramic material and the medium of the intermediate layer 23 is an epoxy resin, the resonant characteristic of the ultrasonic diagnostic apparatus 5 is obtained in the same manner as that shown in FIG. 4. The resonant characteristic of the ultrasonic diagnostic apparatus appears in a manner similar to that shown in FIG. 4 by the dashed line.

Figure 8A:
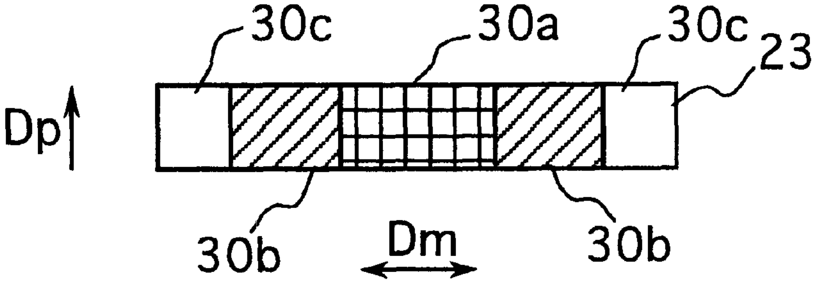
FIG. 8A is an enlarged cross-sectional view of an intermediate layer forming part of the oscillation body shown in FIG. 7 and forming part of the second embodiment of the ultrasonic diagnostic apparatus.

The piezoelectric layers 21 and 22 of the oscillation body 1 have respective cross sections taken on the plane parallel to the wave propagation direction Dp and the azimuthal direction Da as shown in FIG. 8A. As shown in this figure, the intermediate layer 23 of the oscillation body 1 has a high impedance portion 30*a* having a predetermined acoustic impedance Za and extending along the azimuthal direction, a pair of low impedance portions 30*c* having respective acoustic impedance Zc lower than that of the high impedance portion 30*a*, and a pair of intermediate impedance portions 30*b* provided between the high impedance portion 30*a* and the low impedance portions 30*c* in the minor axis direction Dm. The adjacent high, low and intermediate impedance portions 30*a*, 30*c* and 30*b* are integrally formed with one another, and respectively forms different material portions different in acoustic impedance. These portions 30*a*, 30*c* and 30*b* collectively form the intermediate layer 23 as a flat plate. The acoustic impedance of each intermediate impedance portion 30*b* is lower than the acoustic impedance Za of the high impedance portion 30*a* and higher than the acoustic impedance Zc of the low impedance portion 30*c*.

In the present embodiment, the medium of the high impedance portion 30*a* of the intermediate layer 23 is selected to have an acoustic impedance nearly or substantially equal to that of the piezoelectric layer 21 or 22. In contrast, the medium of the low impedance portion 30*c* of the intermediate layer 23 is selected to have an acoustic impedance lower than that of the piezoelectric layer 21 or 22. Therefore, the resonant frequency of the high impedance portion 30*a* is relatively high, while the resonant frequency of the low impedance portion 30*c* is relatively low. The media of the portion 30*a*, 30*b* and 30*c* are different in acoustic impedance from one another. The acoustic impedance of the piezoelectric layer 21 or 22 is set at for example 15 Mrayl or the same degree, and the acoustic impedance of the intermediate layer 23 is set at for example 5 Mrayl or less.

Figure 8B:
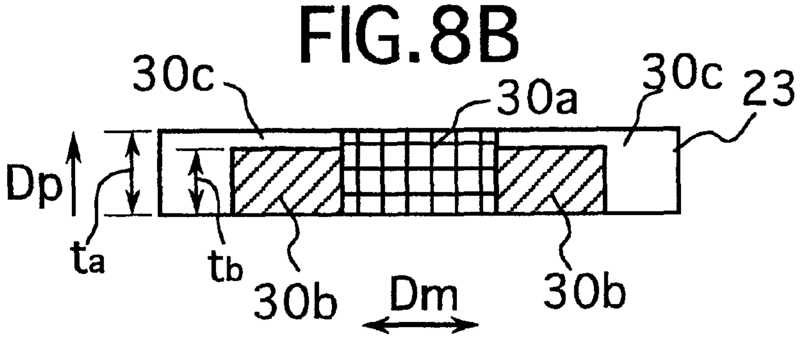
FIG. 8B is an enlarged cross-sectional view of an intermediate layer different in material from the piezoelectric layer shown in FIG. 8A and forming part of the oscillation body shown in FIG. 7.

In FIG. 8B, the medium of each intermediate impedance portion 30*b* and a part of the medium of the low impedance portion 30*c* are overlapped in the wave propagation direction Dp. In the concrete, the high impedance portion 30*a* of the flat intermediate layer 23 have a thin plate portion 30*p* laminated on the intermediate impedance portion 30*b* of the intermediate layer 23. The thickness of the intermediate impedance portion 30*b* is set at a value "tb", and the thickness of the high impedance portion 30*a* is set at a value "ta" Within the area wherein the thin plate portion 30*p* is laminated on the intermediate impedance portion 30*b* of the intermediate layer 23, the intermediate layer 23 has an acoustic impedance higher than that of the low impedance portion 30*c* and lower than that of the high impedance portion 30*a*. The low impedance portion 30*c* is formed by hardening a liquidized resin material after the liquidized resin material is poured into the cavity in which the high impedance portion 30*a* is produced.

Figure 8C:
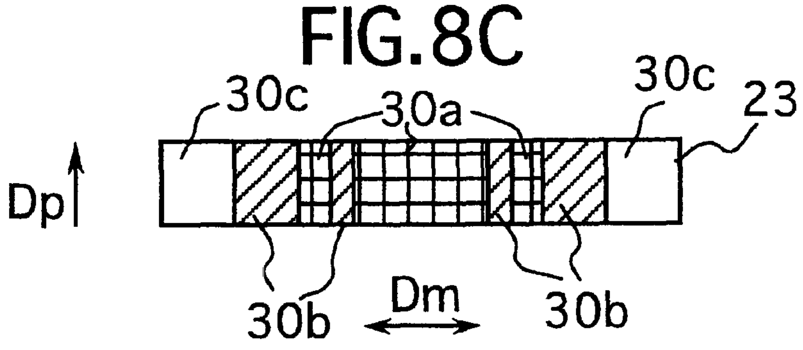
FIG. 8C is an enlarged cross-sectional view of an intermediate layer different in material from the piezoelectric layer shown in FIG. 8A or 8B and forming part of the oscillation body shown in FIG. 7.

As shown in FIG. 8C, the segments 30*a* and 30*b* and the low impedance portion 30*c* are different in medium and integrally formed with one another. The high impedance medium segments 30*a* collectively form a high impedance portion of the intermediate layer 23, and the intermediate impedance medium segments 30*b* as a whole constitute an intermediate impedance portion of the intermediate layer 23. In this case, the resonant frequency is moderately varied at the boundary between the high impedance portion 30*a* and the intermediate impedance portion 30*b* of the intermediate layer 23.

Figure 8D:
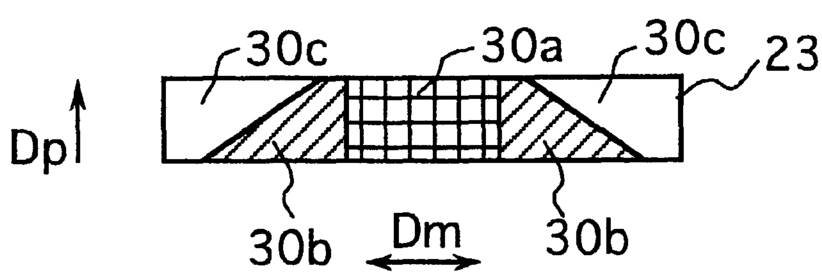
FIG. 8D is an enlarged cross-sectional view of an intermediate layer different in material from the piezoelectric layer shown in FIG. 8A, 8B or 8C and forming part of the oscillation body shown in FIG. 7.

FIG. 8D shows a slanted boundary area wherein the intermediate impedance portion 30*b* and low impedance portion 30 of the flat intermediate layer 23 are overlapped on each other. Within the boundary area, this intermediate layer 23 has an acoustic impedance with the resonant frequency respectively moderately varied in proportion to the ratio of the thicknesses of the intermediate impedance portion 30*b* and the low impedance portion 30*c* of the intermediate layer 23.

Anyone of the above intermediate layers 23 shown in FIG. 8A through 8D is selectively interposed between the piezoelectric layers 21 and 22 of the oscillation body 1 in order to improve frequency characteristic of the oscillation body 1.

Figure 9:
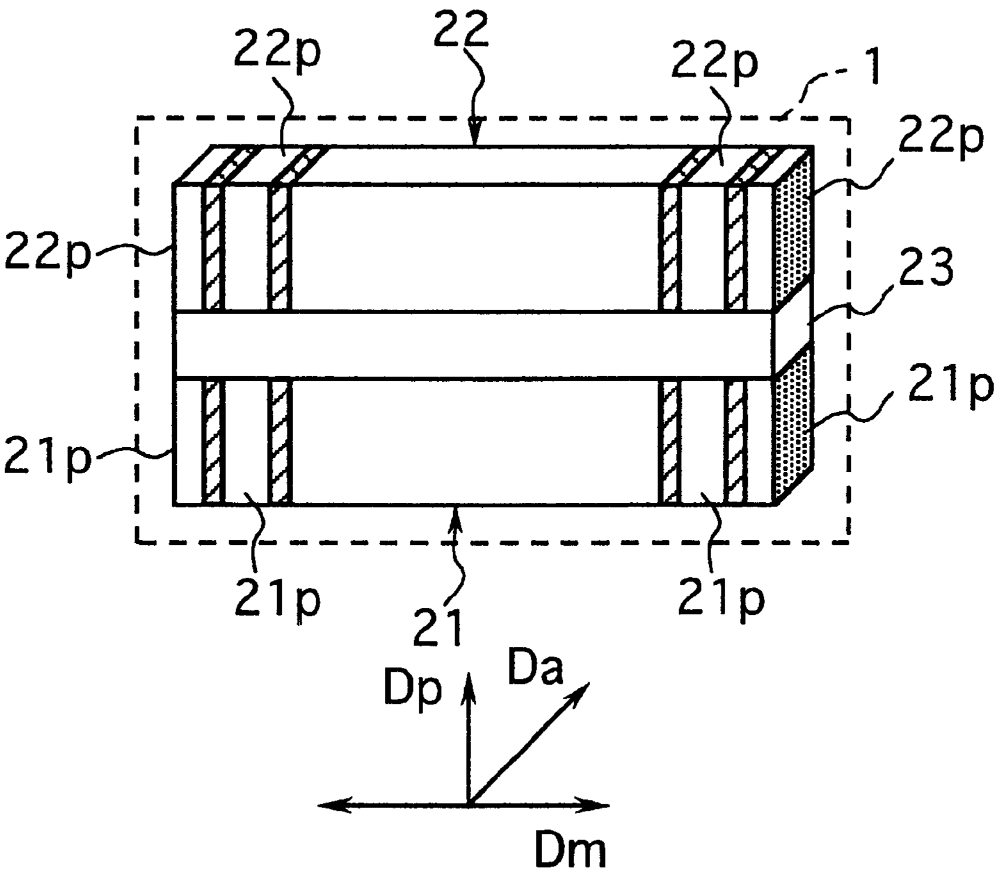
FIG. 9 is a perspective view of a segment forming part of an oscillation body to be replaced with oscillation body shown in FIG. 7.
Figure 10:
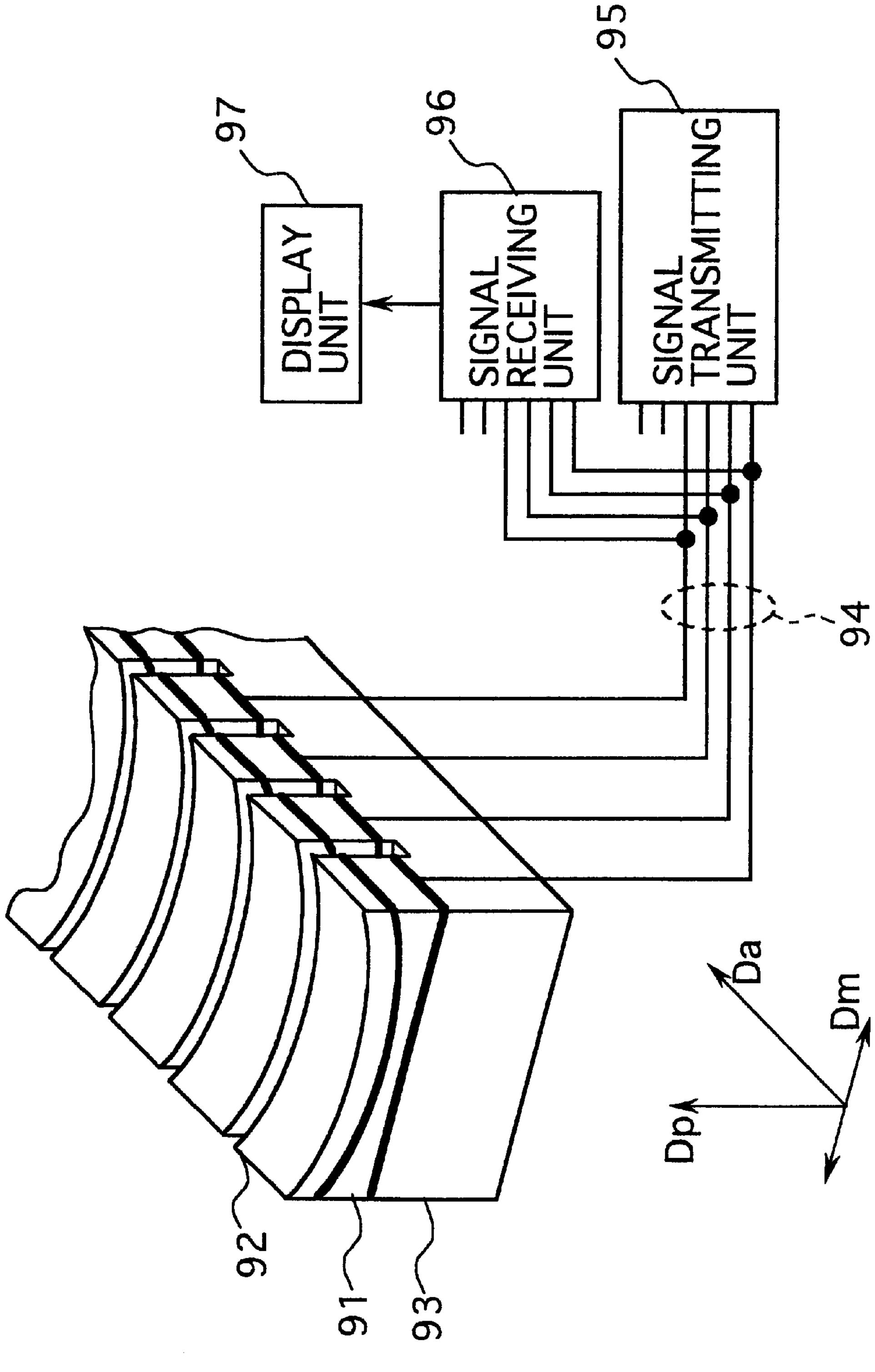
FIG. 10 (PRIOR ART)
FIG. 10 is a schematic diagram of a prior art ultrasonic diagnostic apparatus.

FIG. 9 shows an oscillation body of a third preferred embodiment of the ultrasonic diagnostic apparatus embodying the present invention, and the oscillation body is shown as an oscillation body element forming part of the oscillation body for convenience.

The present embodiment is constructed in the similar manner to the aforesaid second embodiment except for the difference in structure of the piezoelectric layers. For this reason, the following description will be briefly made with the reference numerals partly the same as those of the above constitutional elements of the second embodiments.

The oscillation body 1 has a pair of piezoelectric layers 21 and 22 each divided in the azimuthal direction Da into a plurality of segments to have a set of end pieces 21*p* and 22*p*. This enables the oscillation body 1 to have the elastic compliance of the oscillation body 1 substantially reduced in the azimuthal direction Da so that the resonant frequency of the oscillation body 1 lowers.

In the case that each of the piezoelectric layers 21 and 22 is divided into different set of center and end pieces smaller than those of the above piezoelectric layer 21 or 22, the oscillation body 1 has the resonant frequency lower than that of the above oscillation body. It is therefore possible for the present embodiment to increase the resonant frequency of the center portion of the oscillation body 1 and to decrease the resonant frequency of each end portion of the oscillation body 1. Consequently, the frequency constant of the center portion of the oscillation body 1 is set at a relatively high value, while the frequency constant of each end portion of the oscillation body 1 is set at a relatively low value.

It is therefore possible not only to provide the ultrasonic diagnostic apparatus with the oscillation body 1 readily machinable and aperture controllable, but also to facilitate the machining and adhesive processes of the oscillation body without declining the resolution of the ultrasonic diagnostic apparatus at any focal distance.

The oscillation body may be one piece although the abovementioned oscillation bodies are divided into to the oscillation body elements arranged in the azimuthal direction Da. The oscillation body may have a circular aperture and may be modified into a compound structure including high and low impedance portions.

The present invention has thus been shown and described above with reference to specific embodiments, however, it should be noted that the invention is not limited to the details of the illustrated structures but changes and modifications may be made without departing from the scope of the appended claims.

What is claimed is:

1. An ultrasonic diagnostic apparatus for observing a detectable object to be ultrasonically diagnosed, comprising:

an ultrasonically diagnostic probe unit for emitting ultrasonic waves to said detectable object in response to input pulse signals, and receiving an ultrasonic echo from said detectable object to probe said detectable object;

a signal transmitting unit operatively connected with said ultrasonic diagnostic probe unit to generate said input pulse signals to be transmitted into said ultrasonic waves by said ultrasonically diagnostic probe unit;

a signal receiving unit operatively connected with said ultrasonically diagnostic probe unit for receiving said ultrasonic echo from said detectable object and processing output signals to be converted into an image of said detectable object being observed; and a display unit operatively connected with said signal receiving unit to display said image of said detectable object on the basis of said output signals from said signal receiving unit to ensure an ultrasonically diagnosed state of said detectable object;

said ultrasonically diagnostic probe unit comprising an oscillation body having a pair of piezoelectric layers an intermediate layer sandwiched by said piezoelectric layers, an acoustic lens body operative to focus said ultrasonic waves from said oscillation body and being emitted to and reflected by said detectable object, and a supporting body having said oscillation body mounted thereon to ensure that said detectable object is probed by said oscillation body to be ultrasonically diagnosed with said display unit, said oscillation body has a wave propagation direction along which said ultrasonic waves propagate, an azimuthal direction perpendicular to said wave propagation direction, and a minor axis direction perpendicular to said wave propagation direction and said azimuthal direction, and in which at least one of said piezoelectric layers of said oscillation body has a central portion extending along said azimuthal direction and a pair of end portions and integrally formed with said central portion, said intermediate layer of said oscillation body has a central portion extending along said azimuthal direction and a pair of end portions and integrally formed with said central portion, said piezoelectric layers and said intermediate layer of said oscillation body respectively having thicknesses in said wave propagation direction, total thicknesses of said end portions of said piezo electric layers are smaller than that of said central portions of said piezoelectric layers, and said thickness of each end portion of said intermediate layer is larger than that of said central portion of said intermediate layer, and the thickness of each end portion of said intermediate layer is mechanically equal to that of said central portion of said intermediate layer, and said central portion of said intermediate layer has predetermined acoustic impedance ultrasonically different from that of each end portion of said intermediate layer.

2. An ultrasonic diagnostic apparatus as set forth in claim 1, in which said intermediate layer of said oscillation body has different material portions different in acoustic impedance and adjacent to one another, said different material portions including a high impedance portion having predetermined acoustic impedance and a pair of low impedance portions having respective acoustic impedance lower than that of said high impedance portion.

3. An ultrasonic diagnostic apparatus as set forth in claim 2, in which said intermediate layer of said oscillation body has a pair of intermediate impedance portions each having acoustic impedance lower than that of said high impedance portion and higher than that of said low impedance portion, said intermediate impedance portions being provided between said high impedance portion and said low impedance portion in said minor axis direction.

4. An ultrasonic diagnostic apparatus as set forth in claim 1, in which said intermediate layer is made of a resin.

5. An ultrasonic diagnostic apparatus as set forth in claim 1, in which said oscillation body further includes an acoustic matching layer provided between said acoustic lens and said piezoelectric layer facing to said acoustic lens.

6. An ultrasonic diagnostic apparatus as set forth in claim 5, in which said matching layer serves as the quarter wave plate.

7. An ultrasonic diagnostic apparatus as set forth in claim 1, in which said signal transmitting unit is operative to generate said input pulse signals as impulse signals or chirp pulse signals to be transmitted into the ultrasonic waves by said ultrasonically diagnostic probe unit.

8. An ultrasonic diagnostic apparatus for observing a detectable object to be ultrasonically diagnosed, comprising:

an ultrasonically diagnostic probe unit for emitting ultrasonic waves to said detectable object in response to input pulse signals, and receiving an ultrasonic echo from said detectable object to probe said detectable object;

a signal transmitting unit operatively connected with said ultrasonic diagnostic probe unit to generate said input pulse signals to be transmitted into said ultrasonic waves by said ultrasonically diagnostic probe unit;

a signal receiving unit operatively connected with said ultrasonically diagnostic probe unit for receiving said ultrasonic echo from said detectable object and processing output signals to be converted into an image of said detectable object being observed; and a display unit operatively connected with said signal receiving unit to display said image of said detectable object on the basis of said output signals from said signal receiving unit to ensure an ultrasonically diagnosed state of said detectable object;

said ultrasonically diagnostic probe unit comprising an oscillation body having a pair of piezoelectric layers, an intermediate layer sandwiched by said piezoelectric layers, an acoustic lens body operative to focus said ultrasonic waves from said oscillation body and being emitted to and reflected by said detectable object, and a supporting body having said oscillation body mounted thereon to ensure that said detectable object is probed by said oscillation body to be ultrasonically diagnosed with said display unit, said oscillation body has a wave propagation direction along which said ultrasonic waves propagate, an azimuthal direction perpendicular to said wave propagation direction, and a minor axis direction perpendicular to said wave propagation direction and said azimuthal direction, and in which at least one of said piezoelectric layers of said oscillation body has a central portion extending along said azimuthal direction and a pair of end portions integrally formed with said central portion, said intermediate layer of said oscillation body has a central portion extending along said azimuthal direction and a pair of end portions and integrally formed with said central portion, said piezoelectric layers and said intermediate layer of said oscillation body respectively having thicknesses in said wave propagation direction, total thicknesses of said end portions of said piezoelectric layers are smaller than that of said central portions of said piezoelectric layers, and said thickness of each end portion of said intermediate layer is larger than that of said central portion of said intermediate layer, and said piezoelectric layers of said oscillation body have respective cross sections taken on a plane parallel to said wave propagation direction and said azimuthal direction and each including a truncated convex portion and a rectangular portion integrally formed with said truncated convex portion, said truncated convex portion having a bulged contour constituted by a flat center surface portion and a pair of inclined surface portions having said center surface portion positioned therebetween in said minor axis direction and each inclined to have its first end connected to said center surface portion and its second end connected to the cross sectional contour of said rectangular portion, said center surface portions of said piezoelectric layers being held in buttjoint engagement with each other and said intermediate layer having a pair of wedge portions opposed to each other and outwardly gradually thickening as the corresponding two positions of said wedge portions space apart from each other.

9. An ultrasonic diagnostic apparatus as set forth in claim 8, in which said truncated convex portions of said piezoelectric layers are held in contact with each other at said flat center surface portions of said truncated convex portions.

10. An ultrasonic diagnostic apparatus as set forth in claim 8, in which said piezoelectric layers respectively have one side surface portions formed with a plurality of grooves and the other surface portions opposed to each other, said one side surface portions being segmented into a plurality of element regions with said grooves spaced apart from one another in said azimuthal direction.

11. An ultrasonic diagnostic apparatus as set forth in claim 8, further comprising:

a first lead member electrically connected to the interior surfaces of said truncated convex portions of said piezoelectric layers; and a second lead member electrically connected to both of the exterior surfaces of said piezoelectric layers, one of said first and second lead members being connectable to a ground and the other of said first and second lead members being connectable to said signal transmitting unit and signal receiving unit.

12. An ultrasonic diagnostic apparatus for observing a detectable object to be ultrasonically diagnosed, comprising:

an ultrasonically diagnostic probe unit for emitting ultrasonic waves to said detectable object in response to input pulse signals, and receiving an ultrasonic echo from said detectable object to probe said detectable object;

a signal transmitting unit operatively connected with said ultrasonic diagnostic probe unit to generate said input pulse signals to be transmitted into said ultrasonic waves by said ultrasonically diagnostic probe unit;

a signal receiving unit operatively connected with said ultrasonically diagnostic probe unit for receiving said ultrasonic echo from said detectable object and processing output signals to be converted into an image of said detectable object being observed; and a display unit operatively connected with said signal receiving unit to display said image of said detectable object on the basis of said output signals from said signal receiving unit to ensure an ultrasonically diagnosed state of said detectable object;

said ultrasonically diagnostic probe unit comprising an oscillation body having a pair of piezoelectric layers, an intermediate layer sandwiched by said piezoelectric layers, an acoustic lens body operative to focus said ultrasonic waves from said oscillation body and being emitted to and reflected by said detectable object, and a supporting body having said oscillation body mounted thereon to ensure that said detectable object is probed by said oscillation body to be ultrasonically diagnosed with said display unit, in which said piezoelectric layers of said oscillation body are made of a ceramic material, and said intermediate layer of said oscillation body has acoustic impedance of 2 through 8 Mrayl.

13. An ultrasonic diagnostic apparatus for observing a detectable object to be ultrasonically diagnosed, comprising:

an ultrasonically diagnostic probe unit for emitting ultrasonic waves to said detectable object in response to input pulse signals, and receiving an ultrasonic echo from said detectable object to probe said detectable object;

a signal transmitting unit operatively connected with said ultrasonic diagnostic probe unit to generate said input pulse signals to be transmitted into said ultrasonic waves by said ultrasonically diagnostic probe unit;

a signal receiving unit operatively connected with said ultrasonically diagnostic probe unit for receiving said ultrasonic echo from said detectable object and processing output signals to be converted into an image of said detectable object being observed; and a display unit operatively connected with said signal receiving unit to display said image of said detectable object on the basis of said output signals from said signal receiving unit to ensure an ultrasonically diagnosed state of said detectable object;

said ultrasonically diagnostic probe unit comprising an oscillation body having a pair of piezoelectric layers, an intermediate layer sandwiched by said piezoelectric layers, an acoustic lens body operative to focus said ultrasonic waves from said oscillation body and being emitted to and reflected by said detectable object, and a supporting body having said oscillation body mounted thereon to ensure that said detectable object is probed by said oscillation body to be ultrasonically diagnosed with said display unit, in which said acoustic lens has a first lens portion of a short focal distance and a second lens portion of the focal distance longer than that of said first lens portion, said second lens portion having said first lens portion positioned therein.

14. An ultrasonic diagnostic apparatus for observing a detectable object to be ultrasonically diagnosed, comprising:

an ultrasonically diagnostic probe unit for emitting ultrasonic waves to said detectable object in response to input pulse signals, and receiving an ultrasonic echo from said detectable object to probe said detectable object;

a signal transmitting unit operatively connected with said ultrasonic diagnostic probe unit to generate said input pulse signals to be transmitted into said ultrasonic waves by said ultrasonically diagnostic probe unit;

a signal receiving unit operatively connected with said ultrasonically diagnostic probe unit for receiving said ultrasonic echo from said detectable object and processing unit signals to be converted into an image of said detectable object being observed; and a display unit operatively connected with said signal receiving unit to display said image of said detectable object on the basis of said output signals from said signal receiving unit to ensure an ultrasonically diagnosed state of said detectable object;

said ultrasonically diagnostic probe unit comprising an oscillation body having a pair of piezoelectric layers, an intermediate layer sandwiched by said piezoelectric layers, an acoustic lens body operative to focus said ultrasonic waves from said oscillation body and being emitted to and reflected by said detectable object, and a supporting body having said oscillation body mounted thereon to ensure that said detectable object is probed by said oscillation body to be ultrasonically diagnosed with said display unit, in which said signal receiving unit has a dynamic filter having said output signals passed therethrough and changed from a high frequency range to a relatively low frequency range.

15. An ultrasonic diagnostic apparatus for observing a detectable object to be ultrasonically diagnosed, comprising:

an ultrasonically diagnostic probe unit for emitting ultrasonic waves to said detectable object in response to input pulse signals, and receiving an ultrasonic echo from said detectable object to probe said detectable object;

a signal transmitting unit operatively connected with said ultrasonic diagnostic probe unit to generate said input pulse signals to be transmitted into said ultrasonic waves by said ultrasonically diagnostic probe unit;

a signal receiving unit operatively connected with said ultrasonically diagnostic probe unit for receiving said ultrasonic echo from said detectable object and processing output signals to be converted into an image of said detectable object being observed; and a display unit operatively connected with said signal receiving unit to display said image of said detectable object on the basis of said output signals from said signal receiving unit to ensure an ultrasonically diagnosed state of said detectable object;

said ultrasonically diagnostic probe unit comprising an oscillation body having a pair of piezoelectric layers, an intermediate layer sandwiched by said piezoelectric layers, an acoustic lens body operative to focus said ultrasonic waves from said oscillation body and being emitted to and reflected by said detectable object, and a supporting body having said oscillation body mounted thereon to ensure that said detectable object is probed by said oscillation body to be ultrasonically diagnosed with said display unit, said oscillation body has a wave propagation direction along which said ultrasonic waves propagate, an azimuthal direction perpendicular to said wave propagation direction, and a minor axis direction perpendicular to said wave propagation direction and said azimuthal direction, and in which at least one of said piezoelectric layers of said oscillation body has a central portion extending along said azimuthal direction and a pair of end portions integrally formed with said central portion, said intermediate layer of said oscillation body has a central portion extending along said azimuthal direction and a pair of end portions and integrally formed with said central portion, said piezoelectric layers and said intermediate layer of said oscillation body respectively having thicknesses in said wave propagation direction, total thicknesses of said end portions of said piezoelectric layers are smaller than that of said central portions of said piezoelectric layers, and said thickness of each end portion of said intermediate layer is larger than that of said central portion of said intermediate layer, said central portion of said intermediate layer is constituted by a medium having acoustic impedance substantially equal to that of any one of said piezoelectric layer, and said end portion of said intermediate layer is constituted by a medium having acoustic impedance substantially equal to or less than that of any one of said piezoelectric layer.

* * * * *

UNITED STATES PATENT AND TRADEMARK OFFICE

CERTIFICATE OF CORRECTION

PATENT NO. : 6,572,552 B2
DATED : June 3, 2003
INVENTOR(S) : Hiroshi Fukukita

It is certified that error appears in the above-identified patent and that said Letters Patent is hereby corrected as shown below:

Column 6,
Lines 45 and 48, please delete "lid", and insert therefor -- 11d --.
Line 49, please delete "ii", and insert therefor -- 11 --.

Column 13,
Line 43, please delete "piezo electric", and insert therefor -- piezoelectric --.

Signed and Sealed this

Twenty-first Day of October, 2003

JAMES E. ROGAN
*Director of the United States Patent and Trademark Office*